US011061008B2

(12) United States Patent
Mohnen et al.

(10) Patent No.: US 11,061,008 B2
(45) Date of Patent: Jul. 13, 2021

(54) ARTIFICIAL ANIMAL PROTEIN CLEANING DIAGNOSTIC SYSTEM

(71) Applicant: BIRKO Corporation, Henderson, CO (US)

(72) Inventors: Drew Mohnen, Henderson, CO (US); Tom Espy, Henderson, CO (US); Mike Gangel, Henderson, CO (US)

(73) Assignee: BIRKO Corporation, Henderson, CO (US)

( * ) Notice: Subject to any disclaimer, the term of this patent is extended or adjusted under 35 U.S.C. 154(b) by 0 days.

(21) Appl. No.: 16/436,607

(22) Filed: Jun. 10, 2019

(65) Prior Publication Data

US 2019/0376943 A1 Dec. 12, 2019

Related U.S. Application Data

(60) Provisional application No. 62/682,744, filed on Jun. 8, 2018.

(51) Int. Cl.
G01N 33/12 (2006.01)
G01N 35/00 (2006.01)
G08B 21/18 (2006.01)
A22B 5/00 (2006.01)

(52) U.S. Cl.
CPC ....... G01N 33/12 (2013.01); G01N 35/00871 (2013.01); G08B 21/182 (2013.01); A22B 5/0082 (2013.01); G01N 2035/009 (2013.01); G01N 2035/0091 (2013.01)

(58) Field of Classification Search
CPC ............. G01N 33/12; G01N 35/00871; G01N 2035/009; G01N 2035/0091; G08B 21/182; A22B 5/0082
See application file for complete search history.

(56) References Cited

U.S. PATENT DOCUMENTS

| | | | | |
|---|---|---|---|---|
| 3,192,056 A * | 6/1965 | Williams | ............ | A23B 4/01 426/235 |
| 3,475,179 A * | 10/1969 | Smith | ............ | A23L 13/20 426/641 |
| 5,194,036 A * | 3/1993 | Chevalier | ............ | A22B 5/007 209/3.3 |
| 5,303,708 A * | 4/1994 | Stouffer | ............ | A22B 5/007 600/437 |
| 5,316,003 A * | 5/1994 | Stouffer | ............ | A22B 5/007 600/443 |
| 5,543,325 A * | 8/1996 | Chatzopoulou | ............ | A23B 4/00 424/94.1 |
| 5,617,864 A * | 4/1997 | Stouffer | ............ | A22B 5/007 600/459 |
| 5,944,598 A * | 8/1999 | Tong | ............ | A22B 5/007 382/100 |
| 6,104,827 A * | 8/2000 | Benn | ............ | A22B 5/007 382/110 |
| 6,167,759 B1 * | 1/2001 | Bond | ............ | A22B 5/007 600/437 |
| 6,170,335 B1 * | 1/2001 | Clinton | ............ | A22B 5/007 73/629 |
| 6,198,834 B1 * | 3/2001 | Belk | ............ | A22B 5/007 348/89 |
| 6,587,575 B1 * | 7/2003 | Windham | ............ | G01N 33/12 382/110 |
| 6,912,434 B2 * | 6/2005 | van den Nieuwelaar | ............ | A22B 3/005 452/53 |
| 9,546,968 B2 * | 1/2017 | Cooke | ............ | G06T 11/60 |
| 2004/0115322 A1 * | 6/2004 | Osborn | ............ | A22B 5/0082 426/326 |
| 2004/0236191 A1 * | 11/2004 | Poliska | ............ | A22B 5/0064 600/300 |
| 2004/0241773 A1 * | 12/2004 | Samadpour | ............ | A22B 5/0064 435/7.32 |
| 2005/0112557 A1 * | 5/2005 | Liu | ............ | G01N 33/53 435/5 |
| 2005/0255263 A1 * | 11/2005 | Lee | ............ | A22C 13/0013 428/34.8 |
| 2005/0257748 A1 | 11/2005 | Kriesel et al. | | |
| 2006/0115559 A1 | 6/2006 | Jones, Jr. | | |
| 2008/0200107 A1 | 8/2008 | Christensen et al. | | |
| 2009/0274341 A1 * | 11/2009 | Wilson | ............ | G01N 33/12 382/110 |
| 2009/0274804 A1 * | 11/2009 | Wilson | ............ | G01N 29/0654 426/231 |
| 2010/0075016 A1 * | 3/2010 | Okamoto | ............ | A22B 5/0076 426/647 |
| 2011/0059185 A1 * | 3/2011 | Saefkow | ............ | A23L 3/358 424/600 |
| 2011/0225931 A1 * | 9/2011 | Schmidt | ............ | B65B 55/027 53/407 |

(Continued)

FOREIGN PATENT DOCUMENTS

WO 00/40094 A1 7/2000

OTHER PUBLICATIONS

International Search Report and Written Opinion for International Application No. PCT/US2019/036383, dated Oct. 4, 2019, 12 pages.

Primary Examiner — Nay Tun
(74) Attorney, Agent, or Firm — Magleby, Cataxinos & Greenwood, P.C.

(57) ABSTRACT

A diagnostic system for processing animal carcass, wherein the system comprises an artificial animal carcass that includes a bladder inside; a sensory module under the exterior surface of artificial animal carcass; and a display module operably coupled with the sensory module. The bladder inside the artificial animal carcass is configured to be filled with water at the slaughter facility, so that the weight of artificial carcass is approximately the same as the weight of real carcass to be processed. The sensory module is configured to measure a selected parameter on the surface of artificial animal carcass to be displayed on the display module.

19 Claims, No Drawings

(56) References Cited

U.S. PATENT DOCUMENTS

| | | | |
|---|---|---|---|
| 2013/0164426 A1* | 6/2013 | D'Apuzzo | A23B 4/0053 |
| | | | 426/518 |
| 2016/0069743 A1* | 3/2016 | McQuilkin | G02B 5/201 |
| | | | 356/416 |
| 2019/0045803 A1* | 2/2019 | Richards | A23L 3/3571 |
| 2019/0304339 A1* | 10/2019 | Williams | A22B 5/0094 |

\* cited by examiner

ARTIFICIAL ANIMAL PROTEIN CLEANING DIAGNOSTIC SYSTEM

CROSS-REFERENCE TO RELATED APPLICATIONS

This application claims the benefit of U.S. Provisional Patent Application No. 62/682,744 filed on Jun. 8, 2018, of which is incorporated by reference herein.

FIELD OF THE DISCLOSURE

Embodiments of the present disclosure relate to diagnostic systems for processing food items, such as animal carcasses. Aspects of the disclosure are particularly directed to the diagnostic systems for processing animal carcass that use artificial animal carcass as one of the diagnostic components.

BACKGROUND OF THE DISCLOSURE

At the slaughter facilities, meat animals are killed, skinned, and washed. Subsequently, the animal carcass ("carcass") is suspended from a gambrel held by a wheeled support that is moveable on a rail system for conveyance of the carcass throughout the rest of the processing stages (e.g., wash step, evisceration, splitting the whole carcass into carcass sides, inspection, knife trimming, and weighing) and eventually into the chill storage unit where the carcass is cooled and aged.

Various foreign materials including blood, bone dust, hair, dirt, fecal matter, and contaminating microorganisms are generally adhered to the carcass surfaces. Carcass must be substantially free of all such foreign material in order to exceed the minimum Governmental regulatory standards and to be acceptable for market.

The economic burden of foodborne illnesses in the U.S. has been estimated to be $14 billion or 60,000 QALYs per year. Poultry, pork and beef cause about $5.7 billion or loss of 30,000 QALYs in disease burden annually. Michael B. Batz, Sandra Hoffmann, and J. Glenn Morris, Jr., "*Ranking the Risks: The* 10 *Pathogen-Food Combinations with the Greatest Burden on Public Health*", Emerging Pathogens Institutes, University of Florida, 2011.

It is inevitable that bacteria will contaminate the carcass, some of which could potentially be fetal pathogens such as *E. coli* O157:H7 or *Salmonella*. Therefore, applying antimicrobial intervention to carcass during and after the dressing procedure to effectively remove or minimize bacterial contamination is important. Examples of such antimicrobial intervention are trimming, steam vacuuming, carcass washing, hot water rinse, organic acid rinse, and steam pasteurization.

The general hygiene of animal carcass has long been a concern to the meat-processing industry. There are a number of key events that have played a pivotal role in the increased control of *E. coli* O157:H7 in the U.S. meat supply. The 1992-1993 multistate outbreak of *E. coli* O157:H7 focused everyone's attention on *E. coli* O157:H7 and brought about the enforcement of zero tolerance for *E. coli* O157:H7 by the U.S. Department of Agriculture Food Safety and Inspection Service (FSIS), and a subsequent declaration of *E. coli* O157:H7 as an adulterant in ground beef and trim. This was followed closely by mandated Hazard Analysis and Critical Control Point (HACCP) regulation (CFR, 1996), and later many requirements for in-plant validation of interventions. The U.S. Department of Agriculture (USDA) has implemented new inspection regulations involving hazard analysis critical control points (HACCP) systems and pathogen reduction rules. Further, six non-O157 Shiga toxin-producing *E. coli* (STEC) serogroups were added to the list of adulterants in beef (O26, O103, O111, O145, O45, O121).

Consequently, carcass-decontamination procedures have continued to be investigated and utilized to minimize the risk of bacterial contamination on animal carcass.

These and other challenges in processing animal carcasses are equally problematic in the processing of other food items, such as produce. The present disclosure and descriptions related to animal carcasses apply to the processing of other food items using the same or equivalent sensors and systems to analyze cleaning or decontamination of other food items that require cleaning in commercial operations.

DETAILED DESCRIPTION OF THE DISCLOSURE

Embodiments of the present disclosure relate to diagnostic systems for processing food items. Particular embodiments of the present disclosure related to diagnostic systems for processing an animal carcass, wherein the diagnostic systems comprise an artificial animal carcass that can include a bladder inside, at least one sensory module under or on the exterior surface of artificial animal carcass, and a display module operably coupled with the sensory module.

Where included, the bladder inside the artificial animal carcass is configured to be filled with a fluid (e.g., water) at the slaughter facilities, so that the weight of artificial carcass is approximately the same as the weight of a real carcass to be processed. The sensory module is configured to measure a selected parameter on the exterior surface of artificial animal carcass to be displayed on the display module. In particular embodiments where temperature sensors are used, the bladder and temperature sensor should be separated so as to reduce or eliminate the impact of the bladder fluid temperature on the reading of the temperature sensor.

Throughout the description and the claims, the terms "comprise", "comprises", "comprising" and the like are to be construed in an inclusive sense as opposed to an exclusive or exhaustive sense; that is to say, in a sense of "including, but not limited to." As a non-limiting example, the diagnostic system "comprising" a sensory module is construed as the diagnostic system including at least one sensory module.

The term "animal carcass" or "carcass" as used in this disclosure means the whole body of an animal after exsanguination and before evisceration, or a portion of the animal (e.g., head, tongue, or portions of the whole body of an animal).

The diagnostic system for processing animal carcass of the present disclosure is applicable to various animal carcasses, such as bovine, porcine, equine, caprine, ovine, avian animals, or any other animals commonly slaughtered for food production. Bovine animals include, but are not limited to, buffalo and all cattle, including steers, heifers, cows, and bulls. Porcine animals include, but are not limited to, feeder pigs and breeding pigs. Ovine animals include, but are not limited to, sheep. Caprine animals include, but are not limited to, goats.

After meat animals are killed, skinned and washed, the animal carcass is suspended from a gambrel held by a wheeled support that is moveable on a rail system for conveyance of the carcass throughout the carcass processing stages.

Once suspended on a gambrel rail support assembly, the carcass is typically blown with compressed air to remove any loose hair, debris and foreign contaminants, and then conveyed to a carcass prewash stage. During the prewash stage, the carcass is normally washed with low pressure water that has a typical temperature range of 95° F. to 105° F. (35° C. to 41° C.). The purpose of prewash stage is to remove any remaining hair, debris and foreign contaminants not previously removed by the compressed air.

Thereafter, the carcass is moved on the gambrel rail support assembly to a wash stage for the purpose of reducing bacteria on the carcass surface, as well as further removing any remaining loose hair, debris and foreign contaminants. Several process technologies have been developed and applied in the wash stage to reduce bacteria on the surface of carcass in slaughter facilities. The most common antimicrobial treatments include varying stages of hot water rinse or pasteurization, steam pasteurization, and/or chemical wash.

Prior to the chill stage, the carcass may optionally be subjected to the final trim wash stage. This stage may be a hot water rinse or pasteurization, an acid rinse, a steam pasteurization, or combinations thereof.

The efficacy of wash stage (antimicrobial intervention) and the optional final trim wash stage is impacted by the processing conditions such as time, temperature, pressure, etc. Excessive physical or chemical treatment of carcass can result in lower meat quality and undue economic burden to the slaughter facilities without an increase in product safety.

For hot water rinse or pasteurization, the effectiveness of carcass cleaning depends on several parameters, such as temperature and pressure of the carcass surface that is being washed. When the temperature of carcass surface during pasteurization is too high, the carcass surface may become discolored and unacceptable to consumer, as well as increase an unnecessary operation cost to the slaughter facilities. When the temperature of carcass surface during pasteurization is too low, the carcass surface may not be sufficiently cleansed resulting in meat products that do not comply with the minimum Governmental regulatory standards. When the pressure against the carcass surface during pasteurization is too low, an inadequate number of microbes may be present on the carcass surface. When the pressure against the carcass surface during pasteurization is too high, excessive pressure can push bacteria deep into carcass tissues or damage the carcass tissue. Optimum temperature and pressure of the carcass surface can be readily determined by a person skilled in the art, and will be dependent upon various factors such as a type of animal carcass, slaughter procedure, and the dryness of the carcass surface prior to the treatment. For example, it was reported that spray washes applied at 1.4, 2.1, or 2.8 kPa (200, 300, or 400 psi) were more effective than spray washes at 280 kPa (40 psi) for removing fecal matter and bacteria on beef adipose surfaces. B. M. Gorman, B. J. Morgan, J. N. Sofos, and G. C. Smith, "*Microbiological and visual effects of trimming and/or spray washing for removal of fecal material from beef*", J. Food Prot., 1995, 58 (9), pp. 984-989.

To achieve an adequate antimicrobial control, it is critical that the carcass surface reaches a minimum temperature of 145° F. (63° C.) during the hot water rinse or pasteurization for a minimum residence time to kill bacteria. However, it is a common industry practice to control the temperature of hot water used for the hot water rinse or pasteurization, rather than control the temperature of carcass surface. Generally, a hot water having a minimum temperature of 165° F. (74° C.) is required for the hot water rinse or pasteurization. For example, Barkate et al. reported that the carcass must be sprayed with a hot water of about 203° F. (95° C.) for 10 seconds, in order to raise the temperature of carcass surface to 180° F. (82° C.). M. L. Barkate, G. R. Acuff, L. M. Lucia, D. S. Hale, "*Hot water decontamination of beef carcasses for reduction of initial bacterial numbers*", Meat Science, December 1993, 35(3), pp. 397-401. According to U.S. Pat. No. 5,980,375, the hot water sprayed to the centerline of the hot water pasteurization chamber must be at a temperature of about 165° F. (74° C.) in order to achieve adequate antimicrobial effect on the carcass. Therefore, the incoming hot water needs to be at a temperature of about 180° F. (82° C.) to 195° F. (91° C.). Dickson reported the use of hot water having a temperature of 180° F. (82° C.) for the hot water rinse, in order to raise the temperature of the carcass surface to approximately 149° F. (65° C.). J. S. Dickson, "*Hot Water Rinses as a Bacteriological Intervention Strategy on Swine Carcasses*", Proceedings of The Food Safety Consortium Annual Meeting, Kansas City, Mo., October 1997, available at https://www.extension.iastate.edu/Pages/ansci/swinereports/asl-1606.pdf.

As it is a common practice to control the temperature of hot water (rather than the temperature of carcass surface), care must be taken to ensure that hot water remains at an adequate temperature when it reaches the carcass surface. For instance, a spray-jet water rapidly loses heat by evaporation. Studies have shown that the spray of hot water having a temperature of 194° F. (90° C.) that is placed 30 centimeters away from the carcass, causes the carcass surface to reach the maximum temperature of only approximately 63° C. (145° F.). C. Bailey, "Spray washing of lamb carcasses", *Proceedings of the* 17*th European Meeting of Meat Research Workers*, Bristol. Paper B16, year 1971, pp 175-181. The hot water spray wash cabinet using a hot water of about 93° C. (199° F.) to 94° C. (201° F.) can raise the temperature of carcass surface to the maximum of only about 60° C. (140° F.) to 65° C. (149° F.). There has been a report that the hot water temperature is better maintained when the nozzle is no more than 30 centimeters from the carcass surface because less heat is lost as the hot water travels through the air.

It is also a common industry practice to control the pressure of hot water that is injected from the spray nozzle, rather than the pressure of hot water on the surface of animal carcass. Again, care must be taken to ensure that pressure of hot water remains at an adequate level when it reaches the carcass surface. This is because the pressure of hot water is highest at the opening of the spray nozzle, and continues to decrease the further the hot water travels away from the spray nozzle. As with temperature, it is a good idea to keep the nozzle no more than 30 centimeters from the carcass surface to ensure adequate pressure of hot water on the surface of animal carcass.

For the steam pasteurization, the temperature of carcass surface is raised to approximately from 185° F. (85° C.) to 200° F. (93° C.), thereby killing pathogens with the high temperature. Steam pasteurization is based on the fact that steam at 100° C. (212° F.) has a much higher heat capacity than water at the same temperature. Thus, if steam condenses on the carcass surface, the temperature of that carcass surface rises more rapidly than if it were hot water that was deposited on the carcass surface.

For chemical wash, the carcass is subjected to a liquid spray of antimicrobial chemicals for the purpose of inhibiting bacterial growth and contamination. Examples of the antimicrobial chemicals commonly used for the wash stage of carcass include, but are not limited to, a dilute organic acid solution (e.g., acetic acid, lactic acid, citric acid, peracetic acid, hypochlorous acid, acidified sodium chloride, or mixtures thereof); a solution of chlorine-based compounds (acidified sodium chlorite, chlorine dioxide, sodium hypochlorite); and ozonated water. The type of chemicals (e.g., organic acid, chlorine, etc.), concentration, temperature and application amounts may vary. The temperature of carcass surface, the presence of moisture, and solidification of fat surfaces during cooling are all likely to affect the ability of organic acid treatment to effectively decontaminate the carcass. Therefore, the temperature of the carcass surface is one of the parameters that are critical to the antimicrobial efficacy of chemical wash.

The temperature of the carcass surface must be raised to a certain temperature for a successful antimicrobial intervention, regardless the type of antimicrobial intervention (e.g., hot water rinse or pasteurization, chemical wash, or steam pasteurization).

It is a common practice to control the temperature of the hot water, rather than the temperature of the carcass surface. Further, the temperature of carcass surface is dependent on various factors in addition to the temperature of hot water used in the process, such as the distance between the nozzle spray of hot water and the carcass, the size of carcass, the pressure of the hot water, the initial temperature of hot water, etc. Therefore, controlling the temperature of hot water is not effective as controlling the temperature of carcass surface.

Moreover, it is a common practice to determine the effectiveness of wash stage by coating the carcass with shaving cream, then passing the coated carcass through the wash stage, and visually determining the amount of shaving cream left on the carcass surface. Every section of the carcass surface should be subjected to the wash stage, which indicates by the complete removal of shaving cream from the carcass surface. However, this common practice indicates only which sections of carcass surface have been subjected to the wash stage such that the coat of shaving cream is physically removed. It does not indicate whether particular carcass surface areas have reached the threshold conditions (e.g., surface temperature, chemical load, pH, etc.) required to achieve an adequate antimicrobial effect.

The diagnostic system of present disclosure addresses the aforementioned drawbacks of controlling and verifying the cleaning parameters, by instead measuring and controlling the temperature of carcass surface directly. The present disclosure achieves this by using an artificial animal carcass as one of the diagnostic components to measure and control selected processing conditions, such as the surface temperature of carcass. The artificial animal carcass can include a bladder inside that can be filled with a fluid, so that the weight of artificial animal carcass is approximately the same as the weight of real carcass to be processed. The disclosed diagnostic system also includes a sensory module that is placed under or on the exterior surface of the artificial animal carcass to measure the selected parameter at the exterior surface of artificial animal carcass, such as surface temperature, surface pressure, surface pH, chemical load, etc. Additionally, the disclosed diagnostic system includes a display module that can be operably coupled with the sensory module and display the outcome of measured parameter.

The disclosed diagnostic system comprises an artificial animal carcass that includes a sensory module under the exterior surface of artificial animal carcass, and a display module operably coupled with the sensory module. The diagnostic system may also include a bladder inside the artificial animal carcass that is configured to be filled with a fluid at the slaughter facilities, so that the weight of artificial carcass is approximately the same as the weight of real carcass to be processed to recreate real-world processing conditions, while allowing emptying of the bladder for ease of transport of the system. The sensory module is configured to measure one or more selected parameter(s) on the surface of artificial animal carcass to be displayed on the display module.

The disclosed diagnostic system may be used at various stages of the carcass processing at the slaughter facilities. Non-limiting examples of such processing stages include: the pre-evisceration carcass wash; the antimicrobial intervention of carcass (e.g., heat water rinse or pasteurization of the carcass, the steam pasteurization of carcass, the chemical wash of carcass); the final trim rinse of carcass prior to chilling; or combinations thereof.

In some embodiments, the disclosed diagnostic system may be equipped with various sensory modules to measure any parameters of interest at the exterior surface of the artificial animal carcass. Examples of such parameters include, but are not limited to, surface pH of the carcass, surface temperature of the carcass, pressure against the carcass surface, quantity of specific chemical being applied, residue of chemical left on the carcass surface, bacterial load, viral load, and/or contaminant load. Non-limiting examples of such sensory modules are: pH sensory module, temperature sensory module, pressure sensory module, etc. In some embodiments, the temperature sensory module may include electronic thermometer, infrared thermometer, or both.

The sensing process of the present disclosure can be targeted at a chemical property of a liquid, such as the pH value or the presence of certain compounds within a liquid/vapor environment. A dedicated chemical sensor would employ a chemical interface which, directly or indirectly, selectively reacts with (or adsorbs) the targeted substance and changes its physical properties (e.g., its mass due to adsorbtion). The latter change can be detected by means of suited physical sensors. One such means, for example, would be surface acoustic wave (SAW) sensors.

In some embodiments, the disclosed diagnostic system may further comprise an alarm module operably coupled with the display module. The alarm module may be configured to generate an alert signal, such as loud noise or visual signal, when the selected parameter on the display module is outside the optimum or threshold range. As a non-limiting example, the diagnostic system may comprise an alarm module that generates a loud noise when the surface temperature of the artificial carcass displayed on the display module is lower than 145° F. (63° C.), which is the threshold temperature to achieve an adequate antimicrobial effect on the carcass surface during the hot water rinse or sterilization.

In alternative embodiments, the sensors may be provided that are in communication with other devices through wireless technology, such as, for example, Wi-Fi, microwave, radio, mobile communication, satellite, infrared, Bluetooth, near field communication, antenna systems, etc.

We claim:

1. A diagnostic system for animal carcass processing, comprising:
 an artificial animal carcass;
 at least one sensor located under an exterior surface and within the artificial animal carcass or located on and in contact with and on an exterior surface of the artificial animal carcass;
 a display operably coupled with the at least one sensor;

wherein the at least one sensor is configured to measure one or more selected parameter(s) to be displayed on the display; and a bladder inside the artificial animal carcass configured to be filled with a fluid so that the weight of artificial carcass is approximately the same as the weight of a real carcass to be processed.

2. The diagnostic system of claim 1, wherein the diagnostic system is used during a pre-evisceration carcass wash.

3. The diagnostic system of claim 1, wherein the diagnostic system is used during an antimicrobial intervention of the carcass.

4. The diagnostic system of claim 1, wherein the diagnostic system is used during a heat water rinse or pasteurization of the carcass.

5. The diagnostic system of claim 1, wherein the diagnostic system is used during a steam pasteurization of the carcass.

6. The diagnostic system of claim 1, wherein the diagnostic system is used during a chemical wash of the carcass.

7. The diagnostic system of claim 1, wherein the diagnostic system is used during a final trim rinse of the carcass, prior to chilling the carcass.

8. The diagnostic system of claim 1, wherein the selected parameter to be measured by the sensory include a physical property selected from the group consisting of: surface pH of the carcass, surface temperature of the carcass, surface pressure of the carcass, bacterial load, contaminant load, or quantity of specific chemical.

9. The diagnostic system of claim 1, further comprising an alarm operably coupled with the display, wherein the alarm is configured to generate an alert signal when the selected parameter on the display is outside the specific range.

10. The diagnostic system of claim 9, wherein the alarm is configured to generate an alert signal when the surface temperature of the artificial carcass displayed on the display is lower than 145° F.

11. The diagnostic system of claim 1, wherein the sensory module and the display are operably linked via wireless communication.

12. A method of analyzing the effectiveness of a food processing system comprising:
providing a diagnostic system, comprising:
an artificial animal carcass;
a bladder inside the artificial animal carcass configured to be filled with a fluid so that the weight of artificial carcass is approximately the same as the weight of a real carcass to be processed;
at least one sensor located under an exterior surface and within the artificial animal carcass or located in contact with and on an exterior surface of the artificial animal carcass; and
a display operably coupled with the sensor;
wherein the sensor is configured to measure one or more selected parameter(s) on the surface of the artificial animal carcass to be displayed on the display;
advancing the diagnostic system through a processing station; and
measuring a selected parameter on the exterior surface of the artificial animal carcass.

13. The method of claim 12, wherein the processing station is a pre-evisceration carcass wash.

14. The method of claim 12, wherein the processing station is an antimicrobial intervention system.

15. The method of claim 12, wherein the processing station comprises a hot water rinse or pasteurization system.

16. The method of claim 12, wherein the processing station is a steam pasteurization system.

17. The method of claim 12, wherein the processing station is a chemical wash system.

18. The method of claim 12, wherein the processing station is a final trim rinse system.

19. The method of claim 12, wherein the selected parameter to be measured by the sensor include a physical property selected from the group consisting of: surface pH of the diagnostic system, surface temperature of the diagnostic system, surface pressure of the diagnostic system, bacterial load, contaminant load, or quantity of specific chemical.

* * * * *